(12) United States Patent
Tabata et al.

(10) Patent No.: US 7,147,132 B2
(45) Date of Patent: Dec. 12, 2006

(54) AMPOULES FOR LIQUID ATOMIZER

(75) Inventors: Makoto Tabata, Kyoto (JP); Kei Asai, Otsu (JP); Shinichi Ito, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 435 days.

(21) Appl. No.: 10/744,873

(22) Filed: Dec. 22, 2003

(65) Prior Publication Data

US 2004/0188458 A1 Sep. 30, 2004

(30) Foreign Application Priority Data

Mar. 25, 2003 (JP) ............................. 2003-082232

(51) Int. Cl.
*B67D 5/00* (2006.01)
(52) U.S. Cl. ......................... 222/82; 222/81; 222/83; 222/327; 222/386
(58) Field of Classification Search ............ 222/80–83, 222/86–90, 83.5, 386, 326–327, 340, 402
See application file for complete search history.

(56) References Cited

U.S. PATENT DOCUMENTS

| | | | | |
|---|---|---|---|---|
| 3,410,444 A | * | 11/1968 | Morane | 206/219 |
| 3,739,947 A | * | 6/1973 | Baumann et al. | 222/136 |
| 4,258,713 A | * | 3/1981 | Wardlaw | 604/139 |
| 5,307,953 A | * | 5/1994 | Regan | 222/82 |
| 5,692,644 A | * | 12/1997 | Gueret | 222/80 |
| 5,944,222 A | * | 8/1999 | Fuchs et al. | 222/82 |
| 6,321,942 B1 | * | 11/2001 | Krampen et al. | 222/82 |
| 6,398,074 B1 | * | 6/2002 | Bruna et al. | 222/82 |
| 6,401,987 B1 | * | 6/2002 | Oechsel et al. | 222/321.7 |
| 6,708,846 B1 | * | 3/2004 | Fuchs et al. | 222/82 |
| 6,848,598 B1 | * | 2/2005 | Matthews | 222/83.5 |
| 6,913,208 B1 | * | 7/2005 | Tabata et al. | 239/305 |
| 6,997,357 B1 | * | 2/2006 | Fuchs | 222/386 |

FOREIGN PATENT DOCUMENTS

JP 9-511443 11/1997

* cited by examiner

*Primary Examiner*—Frederick C. Nicolas
(74) *Attorney, Agent, or Firm*—Beyer Weaver & Thomas LLP

(57) ABSTRACT

An ampoule for containing a specified amount of liquid inside to be used for a liquid atomizer has a tubular main body having an open front part including an outlet at one end and an open back part at an opposite end. A piston is inserted into the main body from the open front part in an airtight manner and is slidable axially inside the main body. Another piston is inserted into the main body from the open back part in an airtight manner so as to be slidable axially inside the main body. The two pistons form a reservoir in between for storing a liquid. The forwardly located piston has a weakened part on the side that faces the reservoir. As a sharp member extending from the other piston penetrates this weakened, the reservoir and the outlet become connected and the liquid inside the reservoir is discharged.

17 Claims, 11 Drawing Sheets

AMPOULES FOR LIQUID ATOMIZER

BACKGROUND OF THE INVENTION

This invention relates to ampoules and more particularly to the structure of an ampoule for containing a fixed prescribed quantity of a medicament liquid to be used with a liquid atomizer.

Medicament liquids for a quick relief such as those for relieving the symptoms of asthma must be measured accurately for each dose. In order to prepare an accurately measured amount of a medicament liquid, an instrument such as an injector syringe or a pipette must be used, but it is a very troublesome task for a patient to use such an instrument to prepare an accurately measured dose each time it is to be used. Moreover, many patients are not used to such instruments and may fail to have the intended amount of a medicament liquid to be administered. In the case of a medicament liquid that must be administered by a fixed amount, therefore, it is particularly desirable to have it preliminarily measured and packaged individually.

Japanese Patent Publication Tokuhyo 9-511443 disclosed a liquid ampoule for containing an individually measured prescribed mount of a medicament liquid. Since this container is of the structure having one end closed and adapted to have a piston inserted after being filled with a medicament liquid, it is not possible to store the medicament liquid inside without having any air mixed in under an atmospheric condition. Thus, a method of filling the container under a reduced-pressure condition must be adopted, but this means that a dedicated equipment for reducing pressure is required.

When the stored medicament liquid is discharged out of the ampoule, furthermore, a sharp needle-like member must be inserted into the reservoir part, but since the device according to aforementioned Japanese Patent Publication Tokuhyo 9-511443 is not intended to be used for atomizing a liquid and a relatively large quantity of liquid is intended to be stored and discharged, the amount of the medicament liquid which may be left inside the ampoule or the needle-like instrument and fail to be delivered out does not seem to be considered a serious problem.

The dose of a quick-acting medicament liquid for relieving the symptoms of an asthma patient, for example, may be as small as about 20 microliters and hence the amount of the medicament liquid that may remain inside the ampoule and/or the needle-like instrument presents a serious problem.

SUMMARY OF THE INVENTION

It is therefore an object of this invention in view of the above to provide an ampoule structured so as to be capable of being filled with a liquid without having hardly any air mixed inside even under an atmospheric condition.

Another object of the invention is to provide such an ampoule capable of reducing the amount of liquid left inside when it is discharged out thereof.

An ampoule embodying this invention for containing a specified amount of liquid inside may be characterized as comprising a tubular main body having a first open part including an outlet at a forward end and a second open part at a back end, a forwardly placed first piston which is inserted into the main body from its forward open part in an airtight manner and is slidable in an axial direction of the main body, and a backwardly placed second piston which is inserted into the main body from its backward open part in an airtight manner so as to be slidable in the axial direction of the main body and such that the first piston and the second piston form therebetween a reservoir for storing a liquid therein. The first piston has on its side that faces the reservoir a weakened part that is weaker than the other parts of the piston. The main body also contains a sharp member adapted to penetrate the weakened part of the first piston and to thereby connect the reservoir with the outlet.

For filling an ampoule thus structured with a liquid, the first piston is initially inserted into the main body, the liquid is then poured into the interior of the tubular main body and then the second piston is inserted to the main body. The liquid and the first piston are moved toward the first open part in response to the force with which the second piston is inserted such that the main body can contain the liquid without allowing any air to become mixed in even under an atmospheric condition.

The first piston may preferably comprise a tubular part and a membrane, the tubular part contacting the inner peripheral surface of the tubular main body, the membrane covering one end of the tubular part and being thinner than the tubular part to serve as the aforementioned weakened part. With the first piston thus structured, the aforementioned sharp part can dependably penetrate the first piston through its weakened part. The aforementioned sharp member may be arranged so as to extend from the second piston towards the first piston.

Alternatively, a guide tube may be provided inside the main body, connecting to the outlet and extending from the first open part toward the second piston such that the sharp member is near an end part of the guide tube toward the second piston. The main body may be structured so as to include a guide groove at the outlet, extending forward and being upwardly open. With such a guide groove, the outlet of the ampoule can be brought infinitely close to the object to which the liquid is to be supplied.

It is further preferable to provide positioning means for positioning the ampoule with respect to an external apparatus to which it is adapted to be attached. Such means are convenient in avoiding positioning errors in setting the ampoule to an external apparatus.

It is also preferable to further provide a cover member having protrusions extending inside the main body for causing the second piston to slide toward the first piston. Such a cover member may be disposed on the side of the second open part of the main body. The aforementioned may include first positioning means disposed between the main body and the cover member for positioning the cover member with respect to the main body, and second positioning means disposed on the cover member for positioning the cover member with respect to the external apparatus.

DETAILED DESCRIPTION OF THE INVENTION

The invention will be described next by way of examples. Ampoules, as being used with a medicament liquid atomizer for atomizing a liquid medicament, say, for treating an asthma patient, will be described but it is to be reminded that ampoules according to this invention may be used for liquid atomizers of all kinds adapted to atomize a liquid.

Figure 1:
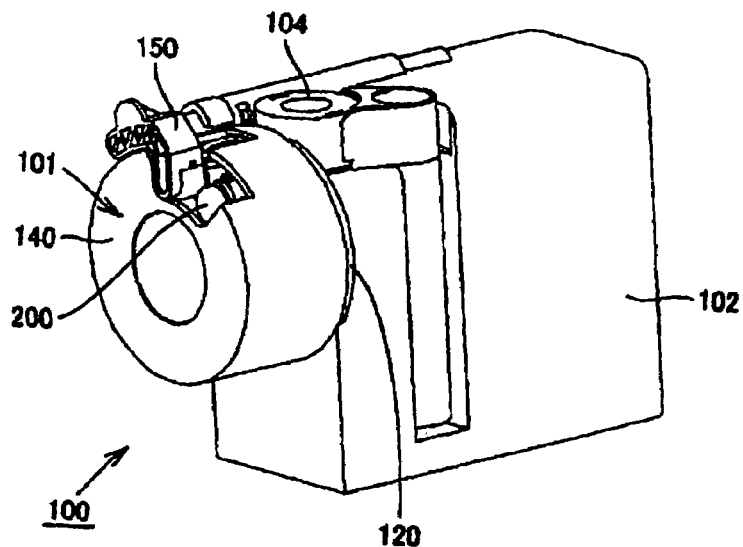
FIG. 1 is a diagonal external view of a liquid atomizer provided with ampoules embodying this invention.
Figure 2:
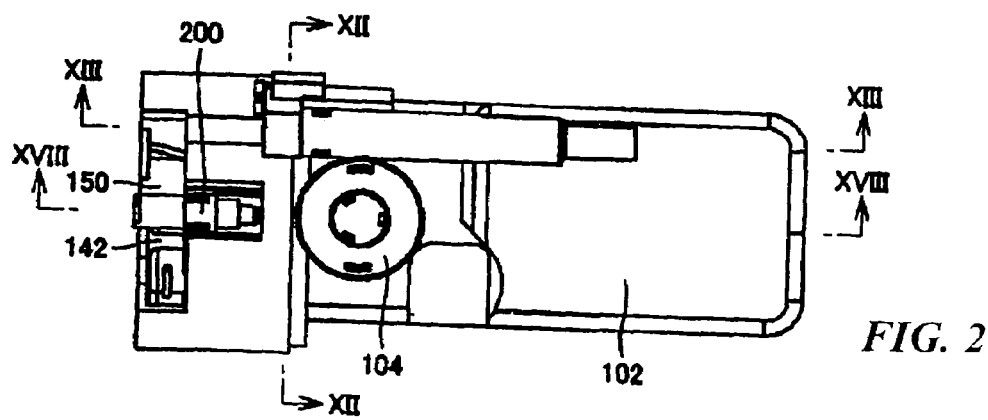
FIG. 2 is a plan view of the liquid atomizer of FIG. 1.
Figure 3:
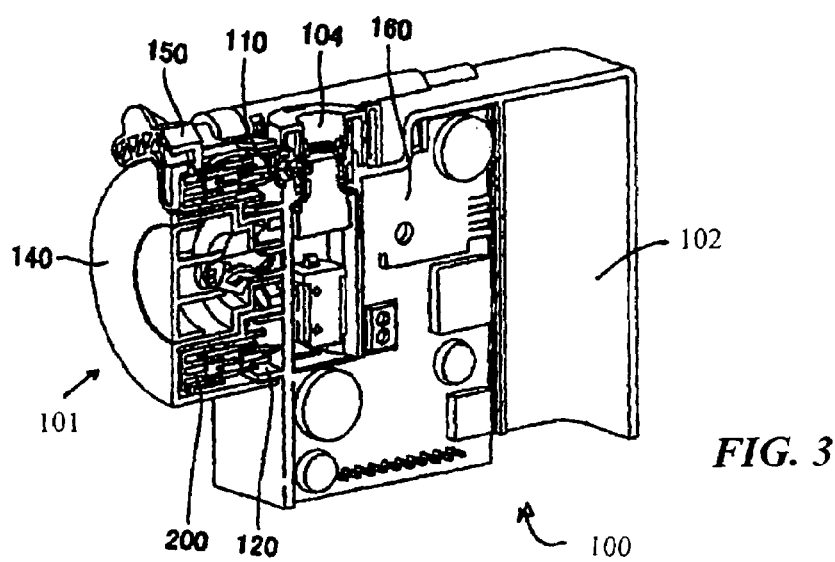
FIG. 3 is a sectional view taken along line XVIII—XVIII of FIG. 2.
Figure 4:
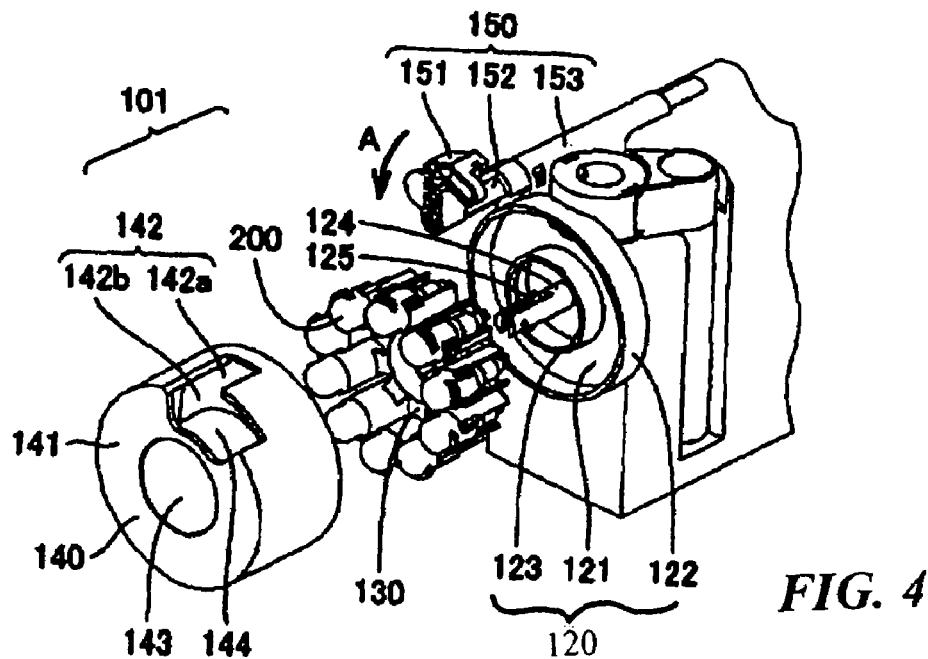
FIG. 4 is a partially exploded view of the liquid atomizer of FIG. 1.
Figure 5:
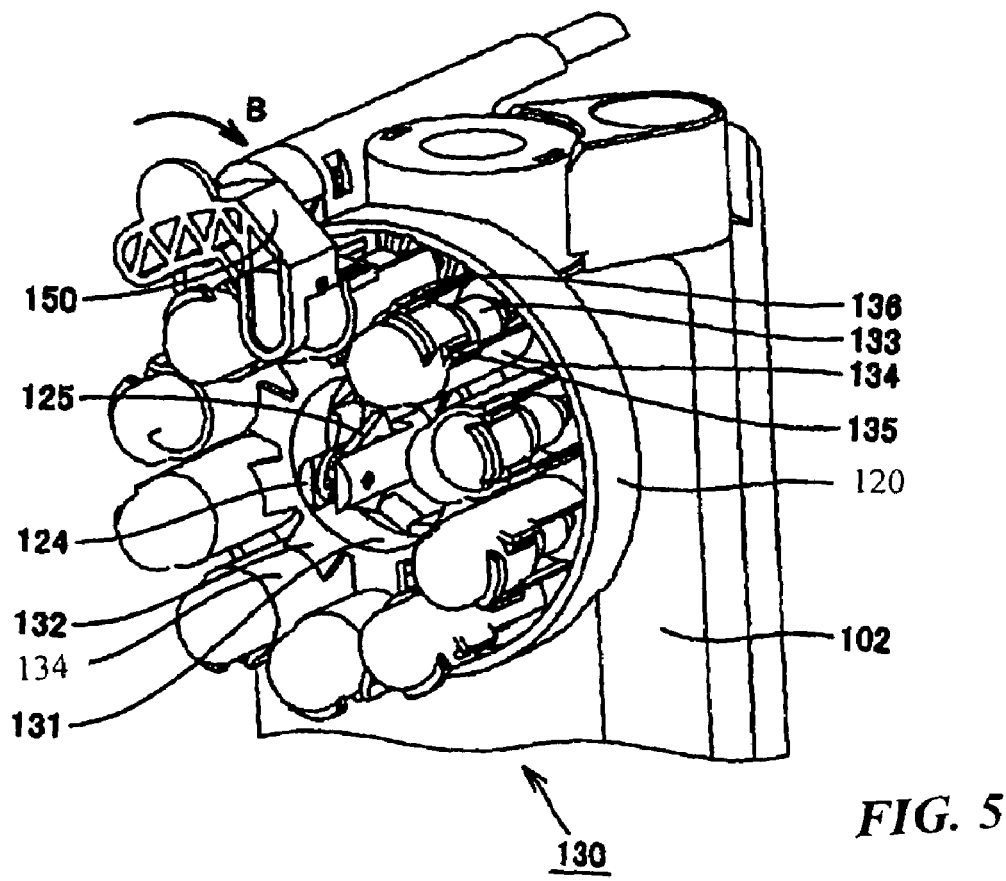
FIG. 5 is an enlarged diagonal view of a portion of the liquid atomizer of FIG. 1.
Figure 6:
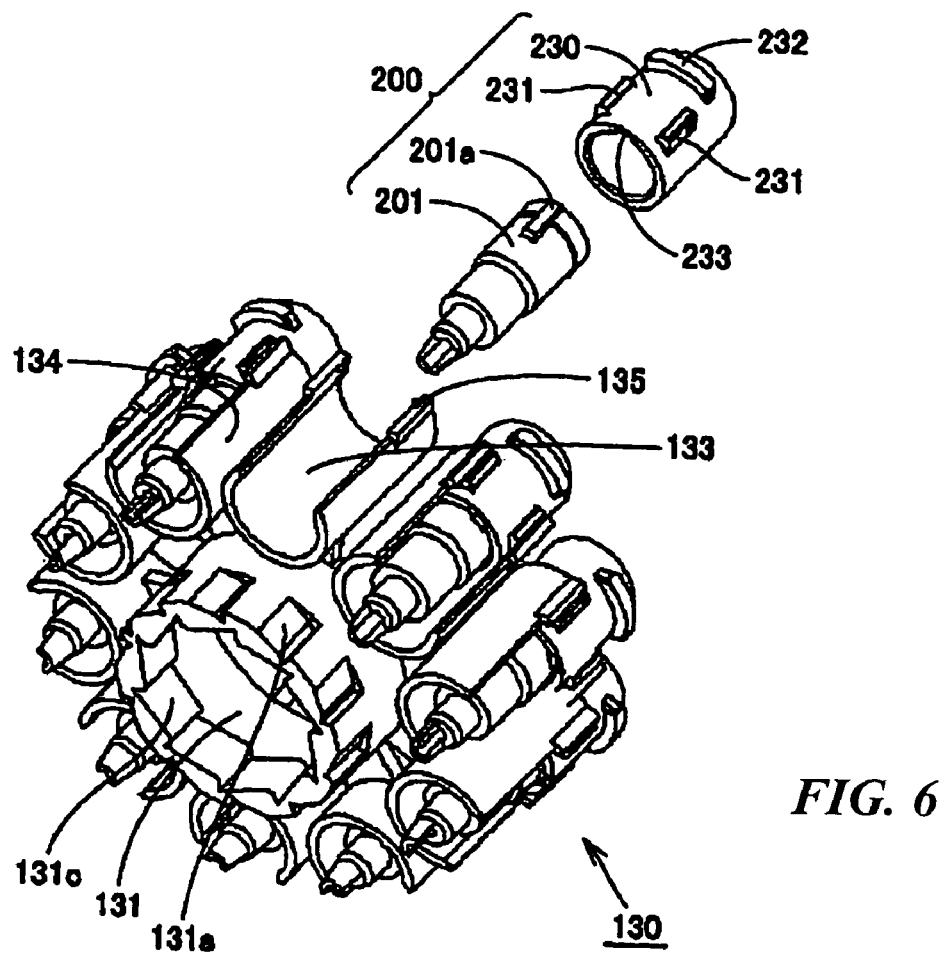
FIG. 6 is an enlarged diagonal view of a rotary ampoule holding member of the liquid atomizer of FIG. 1.

FIGS. 1–6 are referenced first to describe the overall structure of such a medicament liquid atomizer (hereinafter referred to simply as the atomizer) 100. FIG. 1 is its diagonal external view, FIG. 2 is its plan view, FIG. 3 is its sectional view taken along line XVIII—XVIII of FIG. 2, FIG. 4 is its partially exploded view, FIG. 5 is an enlarged diagonal view of a portion thereof, and FIG. 6 is an enlarged diagonal view of its rotary ampoule-holding member (herein referred to as the rotary member 130).

As shown in FIG. 1, the atomizer 100 is comprised of a main frame 102 provided with an atomizing part 104 and an ampoule holder 101 serving as an ampoule holding means disposed near the atomizing part 104 for holding a plurality of ampoules 200 embodying this invention for supplying a medicament liquid to the atomizing part 104. The ampoules 200 are held in an annular formation. As the ampoule holder 101 causes the annular formation of the ampoules 200 while holding the ampoules 200 in the annular formation, the outlets of the individual ampoules 200 can be brought sequentially to a position proximal to the atomizing part 104.

An elongated member (hereinafter referred to as the arm 150) is provided on the upper surface of the atomizer 100 for moving each of the ampoules 200 held by the ampoule holder 101 from a retracted position towards the atomizing part 104 and to an advanced position.

As shown in FIG. 3, a control unit 160 for controlling the atomizing part 104 is contained inside the atomizer 100. A connector opening 110 for inserting the outlet (to be described below) of an ampoule 200 is provided near the atomizing part 104. On the side of the front surface of the atomizer 100 is a holder base 120 for detachably connecting the ampoule holder 101 to the main frame 102. As more clearly shown in FIGS. 4 and 5, the holder base 120 is comprised of a circular base 121, an outer guide 122 which surrounds the circular base 121, an inner guide 123 provided inside the outer guide 122 and a support shaft 124 extending perpendicularly to the front surface of the main frame 102 from the center of the holder base 120. The support shaft 124 is provided with a hook 125 for engaging with a slidable shaft 145 of an ampoule cover (or "the cover 140", to be described below).

The structure of the ampoule holder 101 is described next.

As explained above, the holder base 120 is provided on the side of the front surface of the atomizer 100 to which the ampoule holder 101 is mounted. As shown in FIGS. 5 and 6, a rotary member 130 is provided detachably to the holder base 120. This rotary member 130 is comprised of a tubular base 131, support arms 132 which extend radially from the outer peripheral surface of this tubular base 131, and ampoule holding members (hereinafter "holding members") 134 which are each connected to the tip of a corresponding one of the support arms 132 and disposed in an annular formation.

The rotary member 130 is mounted to the holder base 120 such that the support shaft 124 penetrates the interior of the tubular base 131 and is arranged such that the holding members 134 will rotate as a whole around the support shaft 124 and the outer peripheral surface of the tubular base 131 will slide along the inner surface of the inner guide 123. An opening 133 is provided on the outer peripheral surface of each holding member 134 and a pair of positioning side walls 135 is provided on the outer peripheral surface abutting this opening 133. Although the rotary member 130 is shown with ten holding members 134, the number of the holding members 134 is not intended to limit the scope of the invention. The number of the holding members 134 on the rotary member 130 may be varied according to the needs.

In summary, since the holding members 134 are arranged such that a plurality of ampoules 200 are held in an annular formation, the ampoules 200 can be contained within a relatively small space and a compact atomizer holding many ampoules 200 can be realized according to this invention. Moreover, since a plurality of ampoules 200 can be preliminarily set in the rotary member 130, a plurality of ampoules 200 can be easily set at once on the holder base 120. After medicament liquid from all of the ampoules 200 has been used up, the entire rotary member 130 can be removed from the holder base 120 and another rotary member 130 carrying new ampoules 200 filled with a medicament liquid may be set to the holder base 120 such that the used ampoules 200 can be disposed of neatly and efficiently without getting scattered.

Figure 7:
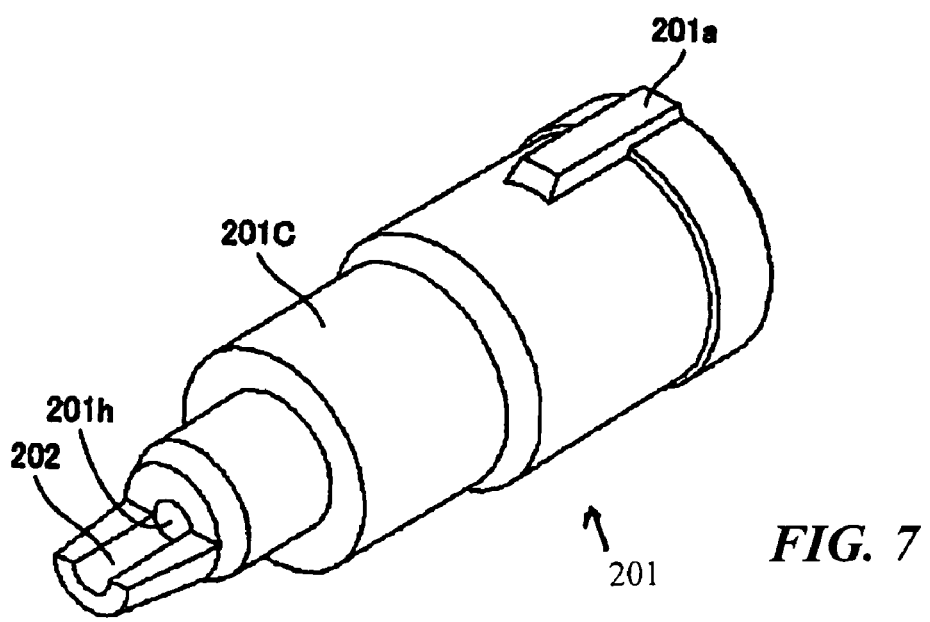
FIG. 7 is a diagonal external view of the main body of an ampoule embodying this invention.
Figure 9:
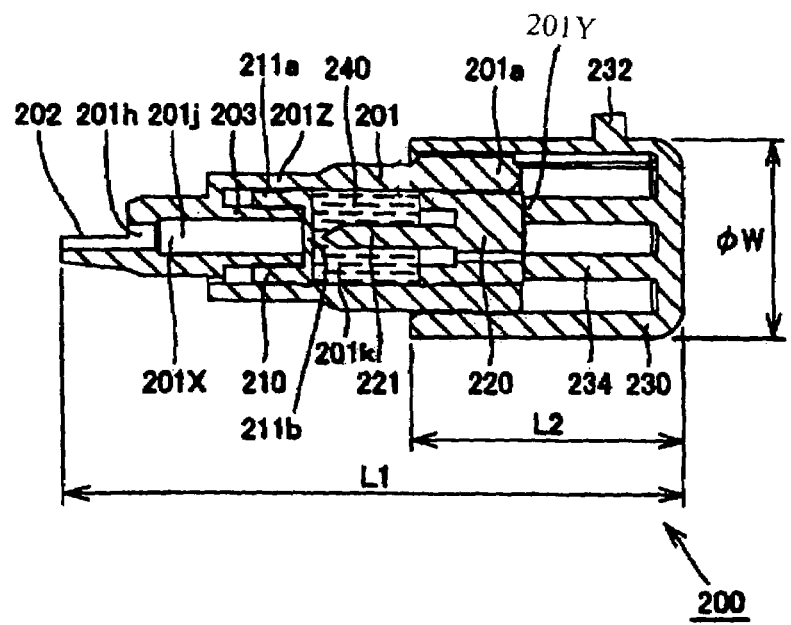
FIG. 9 is a sectional view taken along line IX—IX of FIG. 8 before injection.
Figure 10:
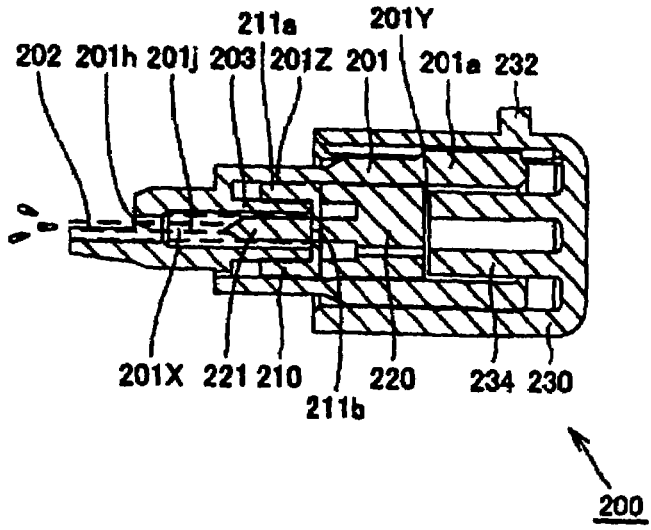
FIG. 10 is a sectional view taken along line IX—IX of FIG. 8 after injection.

The structure of the ampoule 200 is described next with reference to FIGS. 7–11. FIG. 7 is a diagonal external view of an ampoule main body 201 before injection, FIG. 8 is a diagonal external view of an ampoule after injection, FIG. 9 is a sectional view taken along line IX—IX of FIG. 8 before injection, FIG. 10 is a sectional view taken along line IX—IX of FIG. 8 after injection and FIG. 11 (consisting of FIGS. 11A, 11B and 11C) is for schematically showing the functions of the ampoule main body 201.

Figure 8:
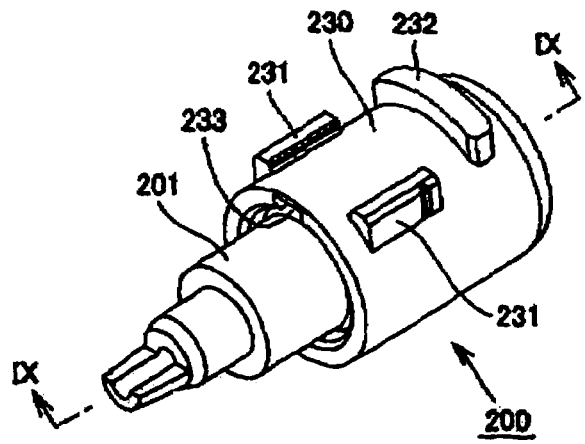
FIG. 8 is a diagonal external view of an ampoule embodying this invention.

As shown in FIGS. 7 and 8, the ampoule 200 is provided with the ampoule main body 201 and a cover member 230 attached to the ampoule main body 201. The ampoule main body 201 is provided with a longitudinally elongated rib 201a on its outer surface and the cover member 230 is provided with a key groove 233 on its inner surface so as to engage with the rib 201a. The rib 201a on the ampoule main body 201 and the key groove 233 on the cover member 230 together serve as a positioning means (hereinafter also referred to as the first positioning means) for dependably positioning the cover member 230 with respect to the ampoule main body 201.

The cover member 230 is also provided with a pair of longitudinally elongated ribs (the first ribs) 231 on its outer peripheral surface such that they will engage with the aforementioned positioning side walls 135 when the ampoule 200 is inserted into the corresponding one of the holding members 134. Thus, the first ribs 230 and the positioning side walls 135 serve as another positioning means (hereinafter also referred to as the second positioning means) for dependably positioning the ampoule main body 134 with respect to the cover member 230.

By way of the engaging relationships described above, the ampoules 200 are capable of sliding longitudinally with respect to the holding members 134 while the ampoule main bodies 201 are prevented from rotating around themselves with respect to the holding members 134. The cover member 230 is also provided with a circumferentially extending rib (the second rib) 232 on its outer peripheral surface at a backward position so as to engage with the arm 150, as will be explained more in detail below.

The structure of the ampoule main body 201 is described next with reference to FIGS. 9 and 10.

The purpose of this ampoule main body 201 is to contain a specified amount (such as about 20 microliters) of a medicament liquid 240 inside. Thus, the ampoule main body 201 comprises an approximately tubular part 201Z having an open part (the first open part 201X) with an outlet 201h at one end and another open part (the second open part 201Y) at the other end.

On the side of the first open part 201X of the tubular part 201Z, there is a piston (the first piston 210) that is inserted into the tubular part 201Z in an airtight manner so as to be slidable in the axial direction of the tubular part 201Z. On the side of the second open part 201Y of the tubular part 201Z, there is another piston (the second piston 220) that is inserted into the tubular part 201Z in an airtight manner so as to be slidable in the axial direction of the tubular part 201Z and to form a reservoir 201k for a medicament liquid 240 between the first piston 210. The first piston 210 is provided so as to cover a tubular portion 211a contacting the inner peripheral surface of the tubular part 201Z and the side of this tubular portion 211a facing the reservoir 201k and includes a weakened part 211b comprising a membrane that is thinner than the average thickness of the tubular portion 211a. The second piston 220 is provided with a needle-like sharp part 221 extending towards the first piston 210.

On the side of the first open part 201X, the tubular part 201Z is provided with a guide groove 202 that extends towards the front and has a cut surface opening in the upward direction. There is also provided a guide tube 203 that forms a passage 201j extending from the side of the first open part 201X towards the first piston 210. Pins 234 are provided inside the cover member 230 for allowing the second piston 220 to slide toward the first piston 210.

If the reservoir 201k is intended to contain 20 microliters of a medicament liquid, as described above, the total length (L1) of the ampoule 200 may be 19.4 mm, the length of the cover member 230 may be 8.6 mm, and the outer diameter (ØW) of the cover member 230 may be 6.3 mm.

If the cover member 230 of the ampoule 200 thus structured is moved in the direction of the first open part 201X, the needle-like sharp part 221 penetrates the weakened part 211b of the first piston 210 such that the reservoir 201k and the passage 201j become connected to each other and it becomes possible to discharge the medicament liquid 240 out of the reservoir 201k. An outlet 201h is formed integrally at one end of the tubular part 201Z.

Figure 11C:
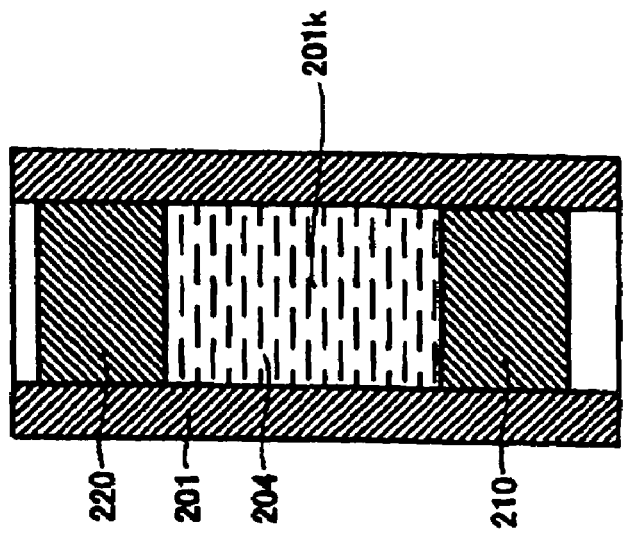
FIGS. 11A, 11B and 11C, together referred to as FIG. 11, are schematic drawings for showing the functions of the ampoule main body of FIG. 7.
Figure 11B:
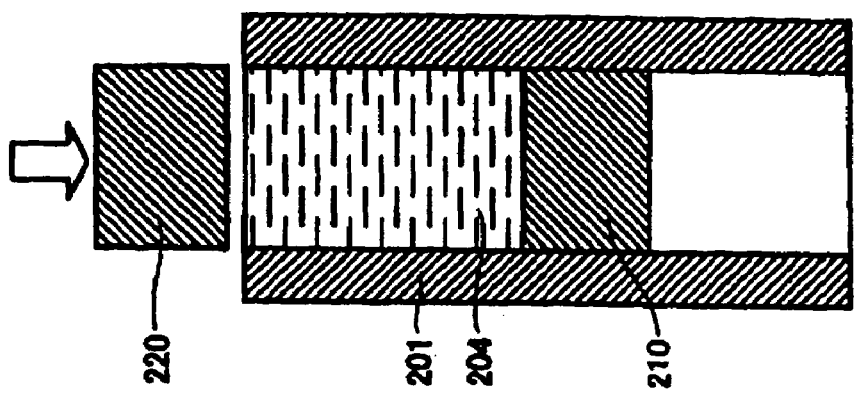
Figure 11A:
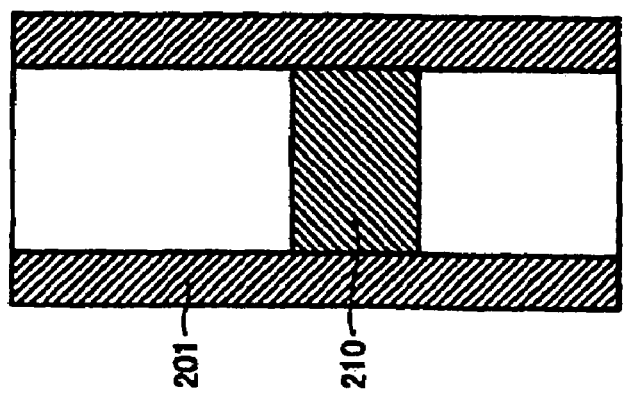

FIG. 11 shows how the ampoule main body 201 of this invention can be filled with the medicament liquid 240. To start, the first piston 210 is inserted from one end of the tubular part 201Z, as shown in FIG. 11A. Thereafter, the medicament liquid 240 is poured in to fill the other side of the first piston 210, as shown in FIG. 11B. Still thereafter, the second piston 220 is inserted from the other end of the tubular part 201Z, as shown in FIG. 11C. Because of the pressure accompanying the insertion of the second piston 220, both the medicament liquid 240 and the first piston 210 are moved slidingly inside the tubular part 201Z. In this manner, the medicament liquid 240 can be stored inside the tubular part 201Z without allowing hardly any air inside the reservoir 201k even under the atmospheric condition.

The structure of the cover 140 is described next. As shown in FIG. 4, the cover 140 is comprised of a tubular main body 141 with a window 142 on its side surface. The window 142 is formed with a first window part 142a extending in the axial direction and a second window part 142b extending in the circumferential direction. The tubular main body 141 is provided at its center part with an inward indentation 144, containing therein an unlocking tube 143 so as to be slidable in the axial direction without becoming separated from the indentation 144.

The function of this unlocking tube 143 is described next with reference to FIG. 18 which is an enlarged sectional view taken along line XVIII—XVIII of FIG. 2, showing only relevant components.

Under the condition where the rotary member 130 and the cover 140 are attached, the rotary member 130 is pressed by the cover 140 in the direction of the holder base 120, and the cover 140 is affixed to the support shaft 124 as the hook 125 on the support shaft 124 engages with an engagement area 145h provided on the slidable shaft 145 of the ampoule cover 140. Under this condition, the cover 140 is pressed in the direction of the holder base 120 such that the rotary member 130 is pressed towards the holder base 120 by the hook 125. Thus, the rotary member 130 and the cover 140 become affixed to the holder base 120.

Figure 18:
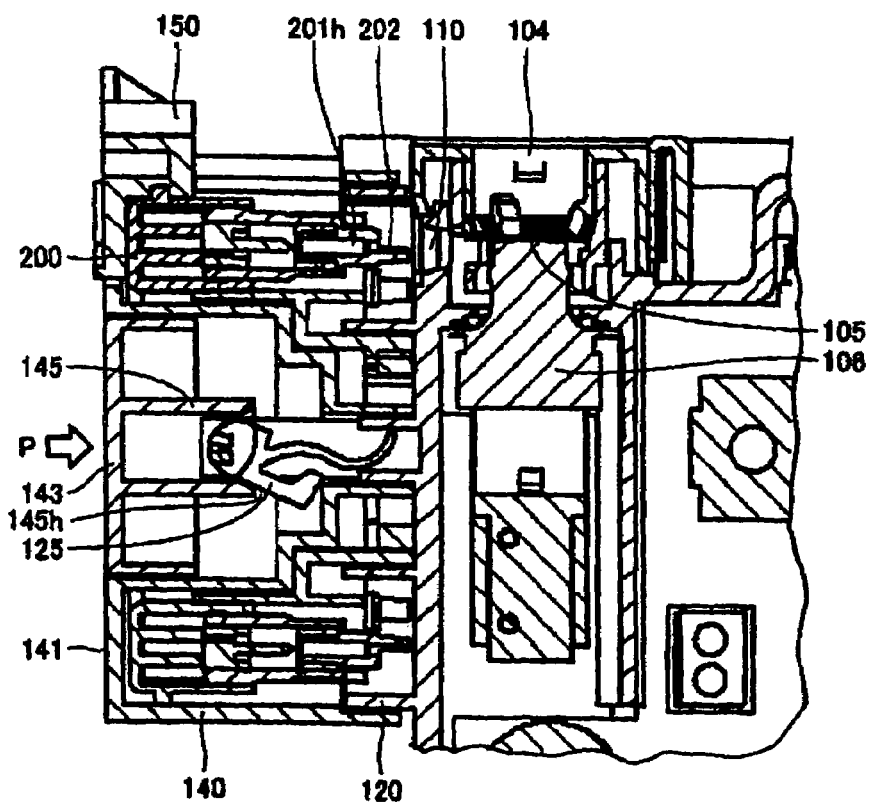
FIG. 18 is a sectional view taken along line XVIII—XVIII of FIG. 2 showing only relevant parts before the injection.

When it is desired to disengage the rotary member 130 from the cover 140, the unlocking tube 143 is inserted in the direction of the holder base 120 (indicated by arrow P in FIG. 18). As a result, the hook 125 is received inside the slidable shaft 145, and the rotary member 130 and the cover 140 are released from the compressive force onto the holder base 120 by the hook 125. Thus, it becomes possible to remove the rotary member 130 and the cover 140.

The rotary mechanism of the ampoule holder 101 is described next with reference to FIG. 12 which is a sectional view taken along line XII—XII of FIG., 2.

The inner guide 123 of the holder base 120 is formed as a combination of two nearly semicircular side walls 123a, one of which being wider than the other. Each of these nearly semicircular side walls 123a is provided with an inwardly protruding ratchet hook 123b or 123c at one end thereof. Since the two side walls 123a are of different widths, neither of the ratchet hooks 123b and 123c is on the straight line connecting the other of the ratchet hooks 123b and 123c and the center of rotation of the ampoule holder 101.

As shown in FIG. 6, furthermore, a plurality of grooves 131a ("the first ratchet grooves") are provided at a specified pitch on the outer peripheral surface of the tubular base 131 of the rotary member 130 adapted to slide along the inner surface of the inner guide 123. Thus, the relationship between the inner guide 123 and the rotary member 130 is such that the rotary member 130 can be rotated in the counter-clockwise direction (hereinafter always as seen from the front side of the rotary member 130 and indicated by arrow C) and that it is prevented from rotating in the clockwise direction (as indicated by arrow D in FIG. 12) because of the directional relationship between the ratchet hooks 123b and 123c and the first ratchet grooves 131a as shown in FIG. 12.

FIG. 6 shows that a plurality of grooves 131c ("the second ratchet grooves") are provided also on the inner peripheral surface of the tubular base 131 at a specified pitch. As shown in FIG. 12, two ratchet hooks 145a are provided on the outer peripheral surface of the slidable shaft 145 of the cover 140. Thus, the relationship between the rotary member 130 and the cover 140 is such that they can rotate together as a single unit in the counter-clockwise direction indicated by arrow C by the engagement between the ratchet hooks 145a and the aforementioned second ratchet grooves 131c but that only the cover 140 can be rotated in the clockwise direction indicated by arrow D because the rotary member 130 is prevented from rotating by means of the inner guide 123.

The numbers of the first and second ratchet grooves 131a and 131c are determined according to the number of the holding members 134. In the example described herein, therefore, there are ten first ratchet grooves 131a and ten second ratchet grooves 131c.

The rotary motion of the holding members 134 controlled by the relationship among the inner guide 123, the tubular base 131 and the cover 140 is described next.

As a first step, the cover 140 is rotated in the counter-clockwise direction by one pitch of the first ratchet grooves 131a. As a result, both the cover 140 and the rotary member 130 rotate simultaneously together by one pitch, transporting one of the holding members 134 on the rotary member 130. Next, as a second step, the cover 140 is rotated in the clockwise direction by one pitch of the second ratchet grooves 131c. Since the rotary member 130 is prevented from rotating in the clockwise direction, it is only the cover 140 that rotates in the clockwise direction by one pitch. Thus, if the first and second steps are sequentially carried out, the holding members 134 are each advanced to the position of the next one.

Figure 12:
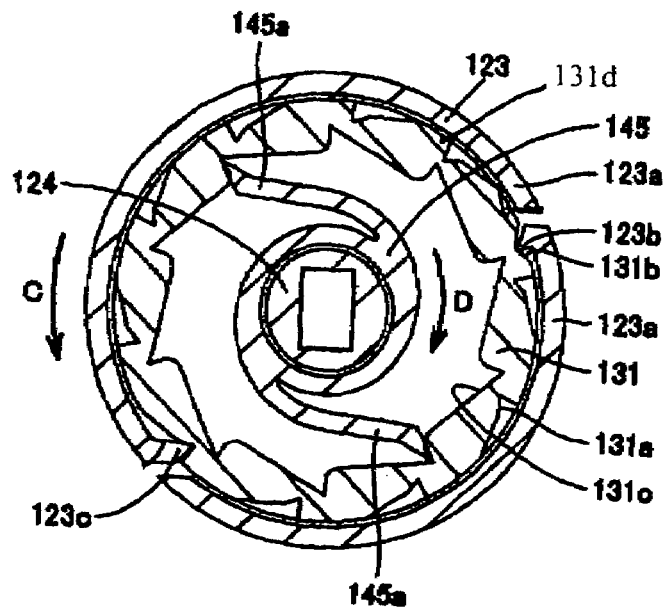
FIG. 12 is a sectional view taken along line XII—XII of FIG. 2.

As shown in FIG. 12, the outer peripheral surface of the tubular base 131 is provided with a positioning groove 131b as means for positioning the rotary member 130 with respect to the holder base 120. This positioning groove 131b is provided at a specified position such that the ratchet hook 123b can be inserted where the ratchet hook 123c engages with the first ratchet groove 131a. Thus, the position for mounting the rotary member 130 with respect to the ratchet hook 123b is uniquely determined. In other words, the initial position at the start of using the ampoules 200 can be uniquely determined.

FIG. 12 shows that the outer peripheral surface of the tubular base 131 is further provided with an indentation ("the final position indicating indentation") 131d. As the rotary member 130 is sequentially rotated in the counter-clockwise direction from its initial position (where the use of the ampoules 200 is started) and after the last of the ampoules 200 has been used up, if the rotary member 130 is further rotated, the ratchet hook 123b comes to be engaged with this indentation 131d and prevents any further rotary motion of the rotary member 130. The ratchet hooks 123b and 123c are individually so shaped that the former can but the latter cannot become engaged with the indentation 131d. By this means, the end position of the use of the ampoules 200 becomes clearly recognizable and the user can easily estimate how soon the rotary member 130 currently being used will have to be replaced by another holder loaded with a new set of unused ampoules 200.

Instead of the final position indicating indentation 131d as described above, or in addition thereto, the last of the holding members 134 to be used may be colored differently such that the user can even more easily estimate how soon the rotary member 130 will have to be replaced next.

The structure of the arm 150 is described next with reference to FIGS. 13 and 14 which are sectional views taken along line XIII—XIII of FIG. 2 at a time before injection and at the time of injection, respectively.

A tubular shaft holder 153 extending in the longitudinal direction is provided on the upper surface of the atomizer main frame 102. The front part of this shaft holder 153 contains therein a slidable shaft 152 so as to be both rotatable around its axis and slidable in the axial direction. A rotatable head 151 is provided on the front side of this shaft holder 153.

This slidable shaft 152 has an indented part 152a formed on its side surface near its back end for engaging and containing a sealing member 152b. An axially elongated hollow part 152c is formed at the back end part of the shaft 152, and a connecting hole 152d is formed for connecting the indented part 152a and the hollow part 152c. Under the condition shown in FIG. 13, this connecting hole 152d is closed by the sealing member 152b.

A piston 156 is disposed behind the shaft 152 inside the shaft holder 153. The piston 156 has a first cylindrical part 156a, a second cylindrical part 156b and a third cylindrical part 156c, the third cylindrical part 156c being between the first and second cylindrical parts 156a and 156b, as shown in FIGS. 13 and 14. A sealing member 158 is engaged on the outer peripheral surface of the third cylindrical part 156c. A coil spring (the first coil spring) 154 is inserted between the shaft 152 and the piston 156, and another coil spring (the second coil spring) 157 is disposed between the back part of the piston 156 and the back end of the shaft holder 153.

Figure 14:
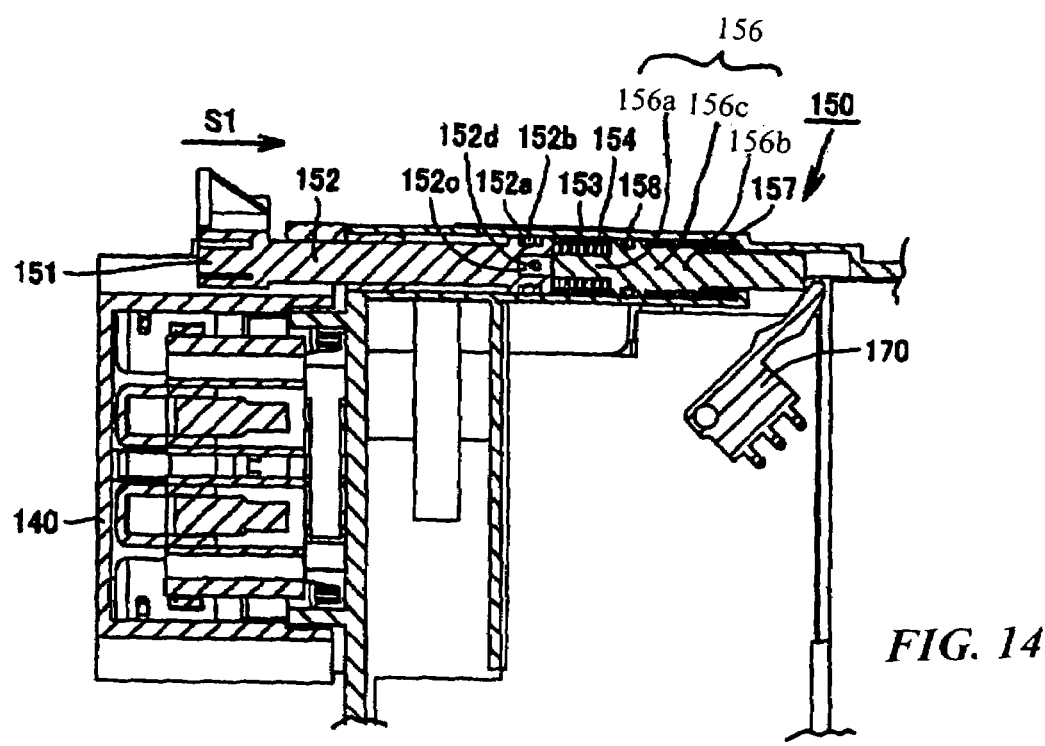
FIG. 14 is a sectional view at the time of injection taken along line XIII—XIII of FIG. 2.

With the arm 150 thus structured, if its head 151 is pushed in, as indicated by arrow S1 shown in FIG. 14, the sealing member 152b moves towards the head 151 in the indented part 152a due to the friction with the inner wall of the shaft holder 153 and the connecting hole 152d comes to a position between the sealing members 152b and 158. Thus, the space containing the first coil spring 154 serves as an air damper, being sealed by means of the sealing members 152b and 158. Thus, the user will feel heavy as the head 151 is initially pushed in and will push it in steadily and slowly. As a result, the ampoule 200 will be made to approach the atomizing part 104 slowly. This is a favorable way of operation because if the medicament liquid is introduced to the atomizing part 104 energetically, it is likely to scatter around and the atomization of the specified quantity of the medicament liquid may not be achieved.

Thereafter, the shaft 152 switches on a limit switch 170 to have the control unit 160 activate the atomizing part 104 such that the medicament liquid will be instantaneously atomized.

Figure 13:
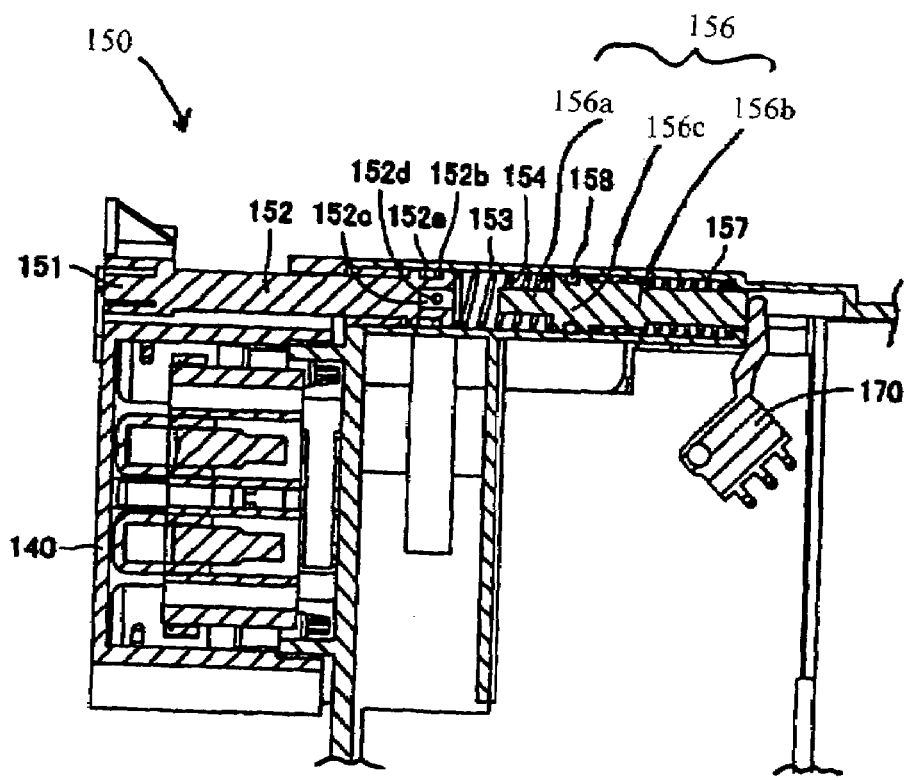
FIG. 13 is a sectional view before injection taken along line XIII—XIII of FIG. 2.

As the compressive force on the head 151 is released, the biasing force of the first and second coil springs 154 and 157 causes the shaft 152 and the piston 156 to return to the positions shown in FIG. 13. At this moment, the sealing member 152b moves towards the back end side of indented part 152a by the friction with the inner wall surface of the shaft holder 153 and the connecting hole 152d connects the space containing the first coil spring 154 with the exterior space.

The structure of the head 151 and its positional relationship with the cover member 230 of the ampoules 200 are described next with reference to FIGS. 15–17.

Figure 15:
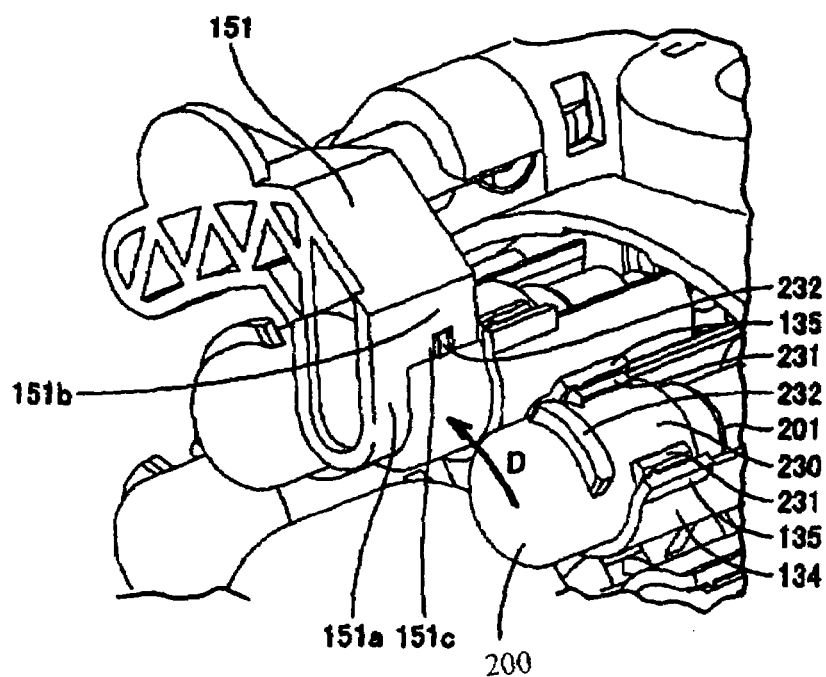
FIGS. 15, 16 and 17 are enlarged diagonal external views for showing the structure of the head and its positional relationship with the cover of the ampoules at different moments.

As shown in FIG. 15, the head 151 is comprised of a vertical part 151a supporting the back part of the cover 230 for the ampoules 200 and a side part 151b positioned at a side of the upper part of the cover 230. A slit 151c is formed at a lower position of the side part 151b in a direction transverse to the axial direction of the shaft 152 so as to be able to accept the aforementioned second rib 232 on the cover 230.

Figure 16:
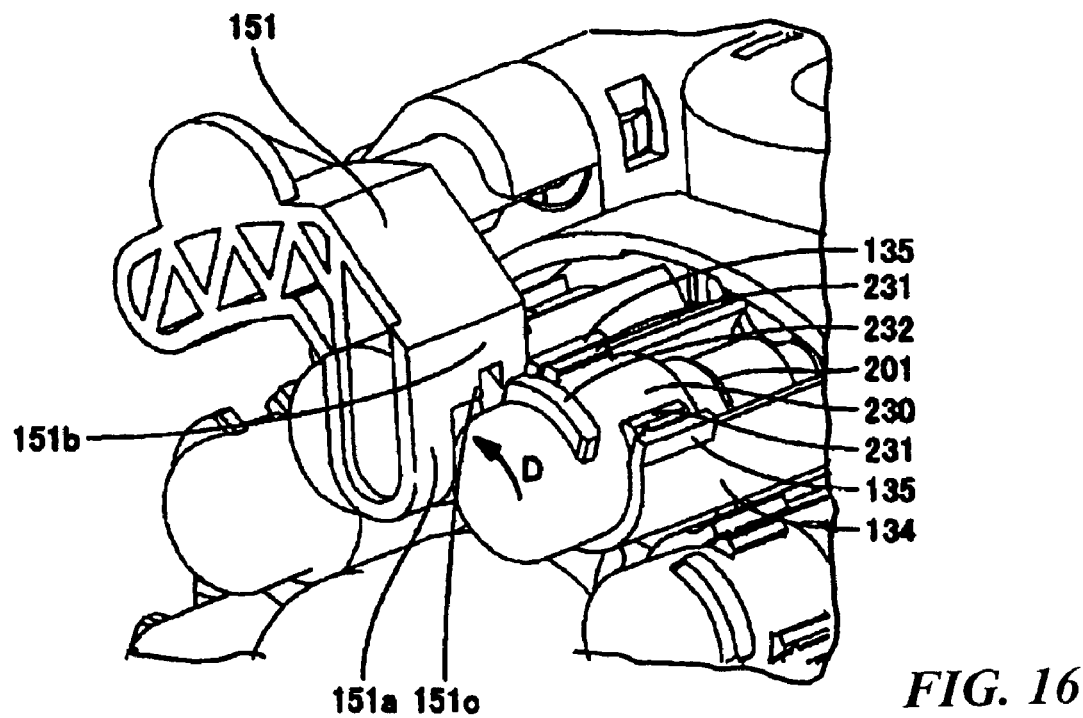
Figure 17:
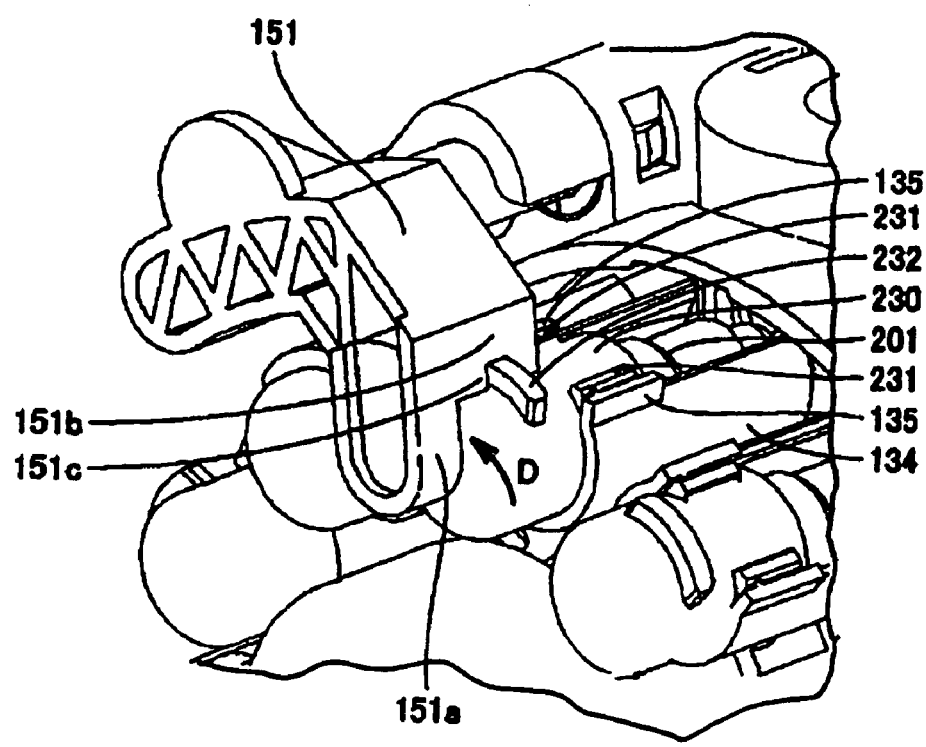

As the rotary member 130 is rotated, the second rib 232 on the cover 230 of the incoming ampoule passes through the space formed by the slit 151c, as shown in FIGS. 16 and 17. Thus, the arm 150 does not interfere with the circular motion of the ampoules 200.

When the second rib 232 associated with one of the ampoules 200 is engaged with the slit 151c, as shown in FIG. 15, as the arm 150 is moved, the outlet 201h of the ampoule 200 can be moved between the advanced position towards the atomizing part 104 as shown in FIG. 14 and the retracted position as shown in FIG. 13 where the rotary member 130 can be rotated with respect to the atomizer main frame 102.

Since the head 151 will interfere with the rotary member 130 when the rotary member 130 loaded with ampoules 200 is mounted to or removed from the holder base 120, the head 151 should be rotated in the direction of arrow D shown in FIG. 15 so as to avoid the interference.

Figure 19:
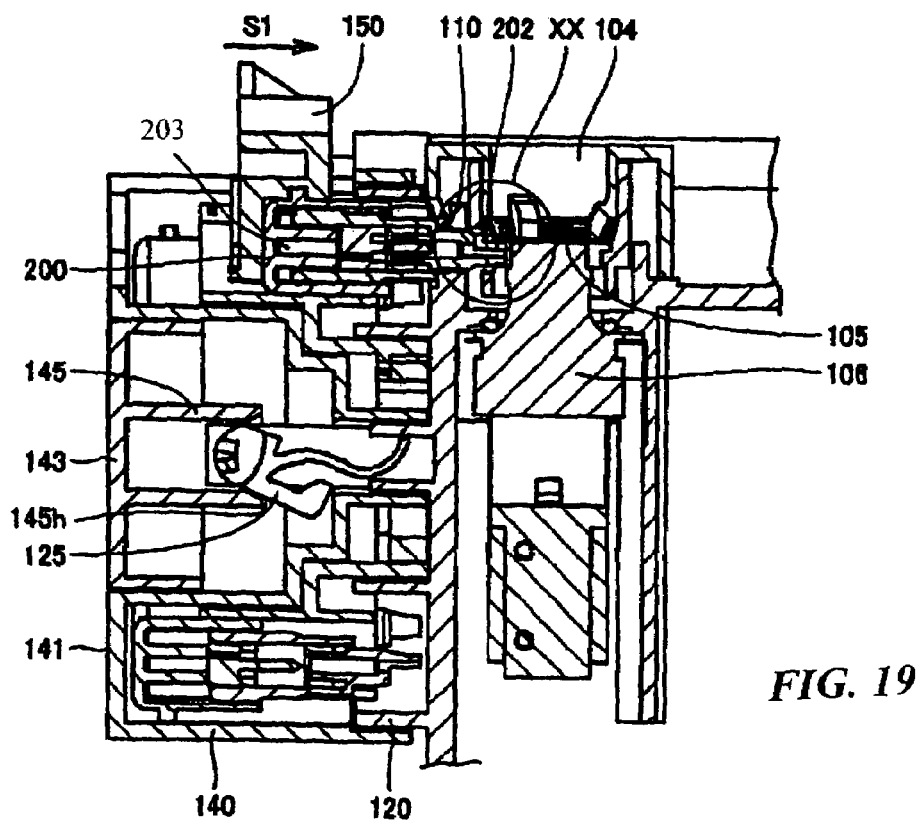
FIG. 19 is a sectional view corresponding to FIG. 18 at the time of injection.
Figure 20:
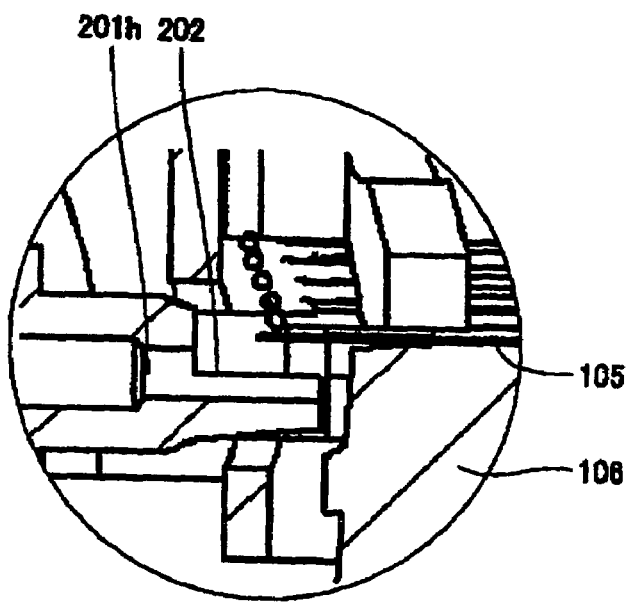
FIG. 20 shows a portion of FIG. 19 indicated by circle XX even more enlarged.
Figure 21:
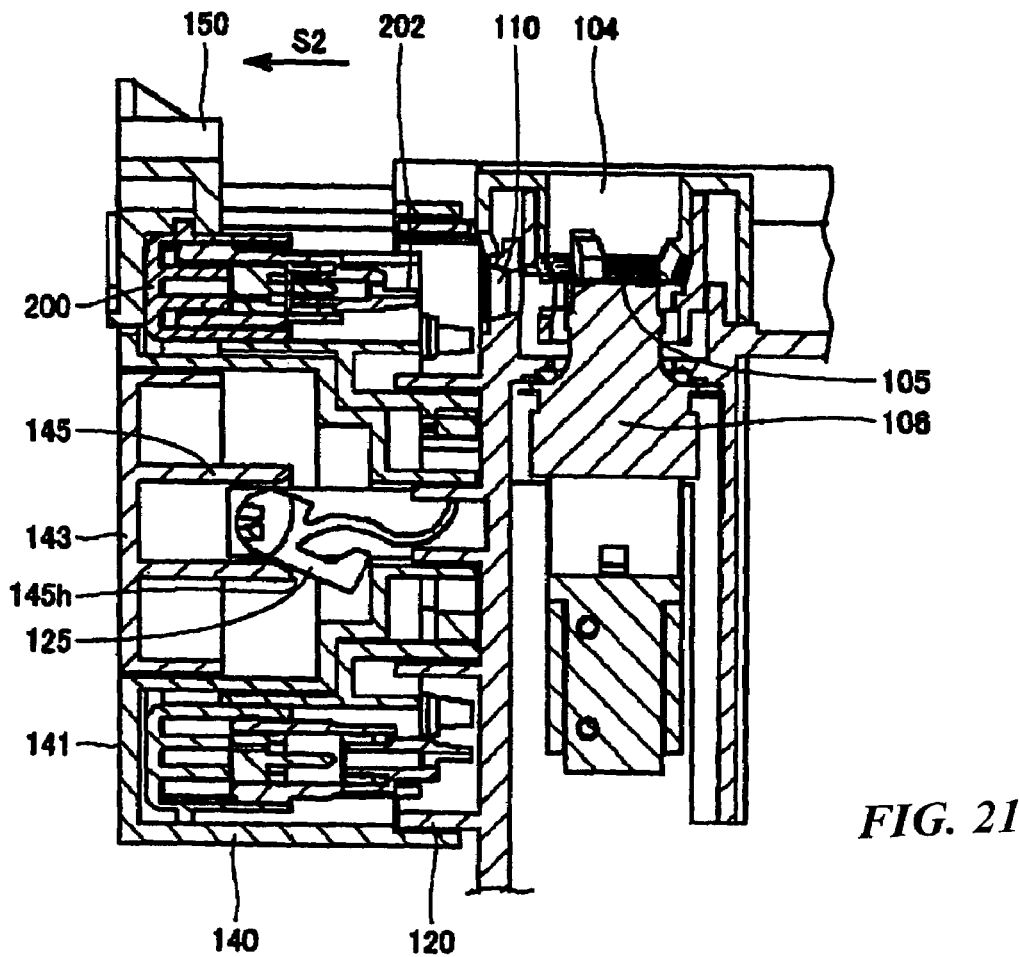
FIG. 21 is a sectional view corresponding to FIGS. 18 and 19 after injection.

The operation of the medicament liquid atomizer 100 thus structured for injection of the medicament liquid is described next with reference to FIGS. 18–21. FIG. 18 is a sectional view taken along line XVIII—XVIII of FIG. 2 showing only relevant parts before injection. FIG. 19 is a corresponding sectional view at the time of injection. FIG. 20 shows a portion of FIG. 19 indicated by circle XX even more enlarged. FIG. 21 is another sectional view corresponding to FIGS. 18 and 19 after injection.

First, the rotary member 130 is rotated such that the outlet 201h of the ampoule 200 filled with a medicament liquid is at a position opposite the connector opening 110 near the atomizing part 104, as shown in FIG. 18. The user can easily ascertain through the window 142 in the cover 140 whether the ampoules 200 are properly mounted or whether they are properly filled with a medicament liquid.

Next, the arm 150 is pushed in the direction of arrow S1, as shown in FIG. 19. As a result, the cover member 230 moves in the direction of the first open part 201X and its pins 234 push the second piston 220 to cause needle-like sharp part 221 to penetrate the weakened part 211b of the first piston 210 such that the reservoir 201k and the passage 201j become connected and the medicament liquid 240 in the reservoir 201k is supplied to the atomizing part 104.

As shown more in detail in FIG. 20, the atomizing part 104 includes a horn vibrator 106 having on its upper surface a mesh 105 that extends sideways. Since the ampoule main body 201 has a forwardly protruding part with the guide groove 202, as explained above with reference to FIG. 7, the outlet 201h can be brought infinitely close to the horn vibrator 106 as the medicament liquid 240 is supplied to the atomizing part 104 and is instantaneously atomized.

The arm 150 is thereafter pulled back in the direction of arrow S2 in FIG. 21. As a result, the ampoule 200 is returned to the interior of the rotary member 130 and hence does not interfere with the rotary motion of the rotary member 130.

As explained above, since a plurality of ampoules 200 are carried in an annular formation, the space for storing them can be made compact. As a result, the ampoule holder 101 can be made compact and hence easily portable. The invention also makes it possible to set a plurality of ampoules 200 at once to the atomizer main frame 102 since the ampoules 200 may be preliminarily set in the rotary member 130. When the medicament liquid in all of the ampoules 200 has been used up, all of the used-up ampoules 200 can be removed at once with the rotary member 130 from the atomizer main frame 102 for replacement. In this manner, the used-up ampoules 200 can be neatly disposed of without getting scattered around.

Since the position of the ampoule 200 to be used first is uniquely determined with reference to the rotary member 130, its position when the last of the ampoules 200 has been used up is also uniquely determined. This makes it easy to estimate how soon the rotary member 130 must be replaced with a new one.

Since the outlet 201h of the ampoule 200 is at a retracted position away from the atomizing part 104 when the rotary member 130 rotates, there is no interference between the outlet 201h and the atomizing part 104. Thus, the atomizing part 104, which is a principal part of the atomizer main frame 102, need not be specially designed and the rotary member 130 can be made rotatable by a simple mechanism.

According to the present invention, furthermore, the medicament liquid 240 can be supplied into the tubular part 201 Z without causing hardly any air to become mixed inside the reservoir 201k. Since the outlet 201h is integrally formed at one end of the tubular part 201Z, the distance of the flow route for the medicament liquid 240 is reduced and the amount of the liquid that may remain inside the tubular part 201Z can be reduced.

Figure 22:
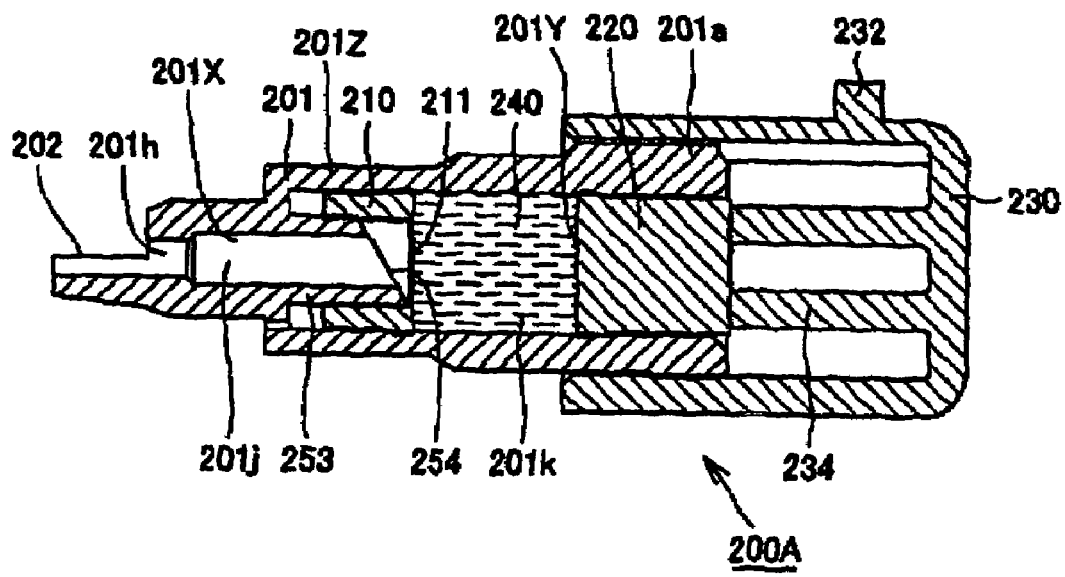
FIG. 22 is a sectional view of another ampoule embodying this invention before injection.
Figure 23:
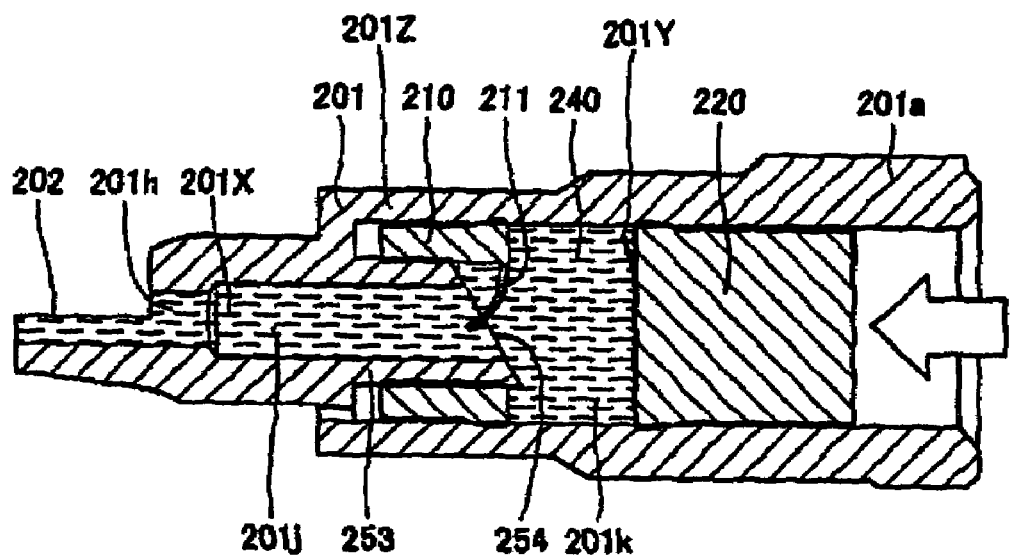
FIG. 23 is a sectional view of the ampoule of FIG. 22 after injection.

FIGS. 22 and 23 show another ampoule 200A according to another embodiment of the invention, FIG. 22 being its sectional view before injection and FIG. 23 being a corresponding sectional view after injection. This ampoule 200A is basically of the same structure as the ampoule 200 according to the first embodiment of the invention described above. The difference is in that the second piston 220 is not provided with any needle-like part (such as the part indicated by numeral 221) but that a sharpened part 254 is provided at the end of a guide tube 253 on the side of the second piston 220, having a tapered surface such that the its width increases from the side of the second piston 220 towards the outlet 201h.

If the amount of the medicament liquid to be stored inside the reservoir 201k is 20 microliters, the external dimensions of the ampoule 200A may be such that the total length L1 is 10.4 mm, the length of the cover member 230 is 8.6 mm and the outer diameter of the cover member 230 is about 6.3 mm.

If the cover member 230 of the ampoule 200A is moved in the direction of the first open part 201X, the first piston 210 moves such that the sharpened part 254 penetrates the weakened part 211b of the first piston 210. The reservoir 201k and the passage 201j thus become connected and the medicament liquid 240 can be discharged out of the reservoir 201k. The second embodiment of the invention described above enjoys the same advantages as the first embodiment of the invention when the medicament liquid is supplied into the ampoule main body 201A.

Although the invention has been described by way of only two embodiments, they are not intended to limit the scope of the invention. Many modifications and variations are possible within the scope of the invention. Although the invention was described above for an application wherein the ampoules are filled with a medicament liquid, the invention is applicable to all situations where a liquid is to be atomized. In summary, the description presented above is intended to be interpreted broadly.

What is claimed is:

1. An ampoule for containing a specified amount of liquid inside, said ampoule comprising:
   a tubular main body having a first open part at one end and a second open part at an opposite end, said first open part including an outlet;
   a first piston inserted into said main body from said first open part in an airtight manner, said first piston being slidable in an axial direction of said main body;
   a second piston inserted into said main body from said second open part in an airtight manner, said second piston being slidable in said axial direction of said main body, said first piston and said second piston forming therebetween a reservoir for storing said liquid therein, said first piston having a weakened part on a side that faces said reservoir; and
   a sharp member penetrating said weakened part and to thereby connect said reservoir with said outlet;
   wherein said main body has a guide groove at said outlet, said guide groove extending forward and being upwardly open.

2. The ampoule of claim 1 wherein said first piston comprises a tubular part and a membrane, said tubular part contacting inner peripheral surface of said main body, said membrane covering one end of said tubular part and being thinner than said tubular part to serve as said weakened part.

3. The ampoule of claim 1 wherein said main body includes a guide tube that connects to said outlet and extends from said first open part towards said second piston.

4. The ampoule of claim 1 wherein said sharp member extends from said second piston towards said first piston.

5. The ampoule of claim 2 wherein said sharp member extends from said second piston towards said first piston.

6. The ampoule of claim 3 wherein said sharp member extends from said second piston towards said first piston.

7. The ampoule of claim 1 wherein said sharp member is near an end part of said guide tube toward said second piston.

8. The ampoule of claim 2 wherein said sharp member is near an end part of said guide tube toward said second piston.

9. The ampoule of claim 3 wherein said sharp member is near an end part of said guide tube toward said second piston.

10. The ampoule of claim 1 further comprising positioning means for positioning said ampoule with respect to an external apparatus to which said ampoule is adapted to be attached.

11. The ampoule of claim 10 further comprising a cover member having protrusions, said protrusions extending inside said main body for causing said second piston to slide toward said first piston, said cover member being on the side of said second open part of said main body, said positioning means including:
    first positioning means disposed between said main body and said cover member for positioning said cover member with respect to said main body; and
    second positioning means disposed on said cover member for positioning said cover member with respect to said external apparatus.

12. An ampoule for containing a specified amount of liquid inside, said ampoule comprising:
    a tubular main body having a first open part at one end and a second open part at an opposite end, said first open part including an outlet;
    a first piston inserted into said main body from said first open part in an airtight manner, said first piston being slidable in an axial direction of said main body;
    a second piston inserted into said main body from said second open part in an airtight manner, said second piston being slidable in said axial direction of said main body, said first piston and said second piston forming therebetween a reservoir for storing said liquid therein, said first piston having a weakened part on a side that faces said reservoir; and
    a sharp member penetrating said weakened part and to thereby connect said reservoir with said outlet;
    wherein said sharp member extends from said second piston towards said first piston.

13. The ampoule of claim 12 wherein said first piston comprises a tubular part and a membrane, said tubular part contacting inner peripheral surface of said main body, said membrane covering one end of said tubular part and being thinner than said tubular part to serve as said weakened part.

14. The ampoule of claim 12 wherein said main body includes a guide tube that connects to said outlet and extends from said first open part towards said second piston.

15. The ampoule of claim 12 wherein said sharp member extends from said second piston towards said first piston.

16. The ampoule of claim 12 further comprising positioning means for positioning said ampoule with respect to an external apparatus to which said ampoule is adapted to be attached.

17. The ampoule of claim 16 further comprising a cover member having protrusions, said protrusions extending inside said main body for causing said second piston to slide toward said first piston, said cover member being on the side of said second open part of said main body, said positioning means including:
    first positioning means disposed between said main body and said cover member for positioning said cover member with respect to said main body; and
    second positioning means disposed on said cover member for positioning said cover member with respect to said external apparatus.

* * * * *